United States Patent [19]

Suh et al.

[11] Patent Number: 4,549,992
[45] Date of Patent: * Oct. 29, 1985

[54] ANTIHYPERTENSIVE AMIDES

[75] Inventors: John T. Suh, Greenwich, Conn.; Jerry W. Skiles, Tuckahoe, N.Y.; Bruce E. Williams, Cottage Grove, Minn.; Alfred Schwab, Williston Park, N.Y.

[73] Assignee: USV Pharmaceutical Corp., Tarrytown, N.Y.

[ * ] Notice: The portion of the term of this patent subsequent to Mar. 17, 1998 has been disclaimed.

[21] Appl. No.: 355,830

[22] Filed: Mar. 8, 1982

Related U.S. Application Data

[63] Continuation-in-part of Ser. No. 200,180, Oct. 24, 1980, Pat. No. 4,304,771, which is a continuation of Ser. No. 57,175, Jul. 13, 1979, Pat. No. 4,256,761.

[51] Int. Cl.$^4$ ............... C07C 153/017; C07D 317/66
[52] U.S. Cl. ........................... 260/455 R; 549/439; 549/480; 549/495
[58] Field of Search ............ 549/69, 76, 439; 424/275, 246, 319, 311, 282; 544/581; 260/455 R, 455 B; 560/16, 17, 9, 125, 155, 153; 562/507, 556, 426

[56] References Cited

U.S. PATENT DOCUMENTS

| | | | |
|---|---|---|---|
| 3,869,492 | 3/1975 | Biel et al. | 260/455 R |
| 4,053,651 | 10/1977 | Ondetti et al. | 260/455 R |
| 4,091,024 | 5/1978 | Ondetti | 260/455 R |
| 4,116,962 | 9/1978 | Ondetti et al. | 260/455 R |
| 4,256,761 | 3/1981 | Suh et al. | 260/455 R |
| 4,304,771 | 12/1981 | Suh et al. | 424/275 |

FOREIGN PATENT DOCUMENTS

| | | | |
|---|---|---|---|
| 2717548 | 4/1977 | Fed. Rep. of Germany | 260/455 R |
| 2753824 | 12/1977 | Fed. Rep. of Germany | 260/455 R |
| 3025856 | 7/1980 | Fed. Rep. of Germany | 260/455 R |
| 1500576 | 4/1974 | United Kingdom | 260/455 R |
| 1577415 | 5/1976 | United Kingdom | 260/455 R |

Primary Examiner—Henry R. Jiles
Assistant Examiner—Robert C. Whittenbaugh

[57] ABSTRACT

Compounds of the structure:

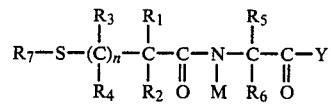

wherein $R_1$, $R_2$, $R_3$, $R_4$, $R_5$, and $R_6$ are independently hydrogen, alkyl, alkenyl, alkynyl, phenyl-alkyl, or cycloalkyl, n is an integer from 0 to 4 inclusive, M is alkenyl, alkynyl, cycloalkyl, cycloalkyl-alkyl, polycycloalkyl, polycyclo-alkyl-alkyl, aryl, aryalkyl, heteroaryl, heteroaryl-alkyl, hetero-cycloalkyl, heterocycloalkyl-alkyl, alkoxyalkyl, alkylthioalkyl, alkylamino-alkyl, dialkylaminoalkyl, fused aryl-cycloalkyl, fused aryl-cycloalkyl-alkyl, fused hetero-aryl-cycloalkyl, or fused heteroaryl-cycloalkyl-alkyl, Y is hydroxy, alkoxy, amino, or substituted amino, amino-alkanoyl, aryloxy, aminoalkoxy, or hydroxyalkoxy, and $R_7$ is a group of the formula

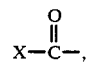

wherein X is a branched alkane or cycloalkyl;

and where Y is hydroxy their non-toxic, pharmaceutically acceptable alkali metal, alkaline earth metal, and amine salts.

The compounds of this invention and their salts possess antihypertensive and angiotensin converting enzyme inhibitory activity.

16 Claims, No Drawings

ANTIHYPERTENSIVE AMIDES

This is a continuation-in-part of U.S. patent application Ser. No. 200,180 filed Oct. 24, 1980, now U.S. Pat. No. 4,304,771 which was a continuation of U.S. patent application Ser. No. 57,175, filed July 13, 1979, now U.S. Pat. No. 4,256,761.

This invention relates to new chemical compounds having valuable pharmaceutical activity. It particularly relates to amides having antihypertensive and angiotensin converting enzyme inhibitory activity and of the structure

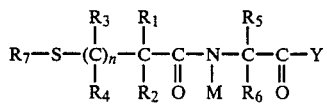

wherein $R_1$, $R_2$, $R_3$, $R_4$, $R_5$, and $R_6$ are independently hydrogen, alkyl, alkenyl, alkynyl, phenyl-alkyl, and cycloalkyl, and may be the same or different.

n is an integer from 0 to 4 inclusive,

M is alkenyl, alkynyl, cycloalkyl, cycloalkyl-alkyl, polycycloalkyl, polycycloalkyl-alkyl, aryl, aralkyl, heteroaryl, heteroaryl-alkyl, hetero-cycloalkyl, heterocycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl.

Y is hydroxy, alkoxy, amino or substituted amino, amino-alkanoyl, aryloxy, aminoalkoxy, or hydroxyalkoxy, and $R_7$ is a group of the formula

wherein X is a branched alkane or cycloalkyl;

and where Y is hydroxy, their non-toxic, pharmaceutically acceptable alkali metal, alkaline earth metal, and amine salts.

The alkyl groups per se and in the alkyl moiety in aralkyl, cycloalkyl-alkyl, polycycloalkyl-alkyl, heteroaryl-alkyl and the like, and, in alkoxy, alkylthio, alkanoyl, carbalkoxy, and alkylamino, may be straight-chained or branched and are preferably lower alkyl groups containing from 1 to 6 carbons. Such groups include methyl, ethyl, propyl, isopropyl, butyl, isobutyl, amyl, iso-amyl, hexyl, and the like.

The alkenyl and alkynyl groups may also be branched or straight-chained and contain from 2 to 6 carbon atoms. Such groups include vinyl, ethynyl, propenyl, allyl, isopropenyl, and the like.

The M cycloalkyl, polycycloalkyl, aryl, heteroaryl, arylalkyl, fused aryl-cycloalkyl groups and the like contain from 3 to 16 carbon atoms and may carry substituents such as lower alkyl, alkenyl, alkynyl, hydroxy, thio, amino, alkoxy, alkylthio, alkyl-amino, and halo. They include such radicals as cyclopropyl, cyclobutyl, cyclopentyl, cyclohexyl, cycloheptyl, adamantyl, norbornyl, phenyl, tolyl, benzyl, phenthyl, dimethoxy-phenyl, hydroxybenzyl, idanyl, naphthyl, tetrahydronaphthyl, decahydronaphthyl, pyridyl, quinolyl, pyrrolidyl, pyrrolyl, morpholinyl, furyl, furfuryl, tetrahydrofurfuryl, benzimidazolyl, thienyl, imidazolyl, and the like.

The preferred compounds are those wherein $R_1$, $R_3$, $R_4$, $R_5$ and $R_6$ are hydrogen, $R_2$ is lower alkyl, preferably $C_1$–$C_3$, more preferably methyl, n is 1, and Y is hydroxy.

$R_7$ is a branched group of the formula

Wherein X is a branched alkane or cycloalkyl, preferably having 4 to 12 carbons and, more preferably, 4 to 8 carbons. Such groups include tert-butyl; 2,2-dimethylpropyl; dimethylbutyl; 2,5-dimethyloctanyl; 2,2,6,6-tetramethyldecanyl; 2-isopropylpentyl; 3,3-dimethylheptyl; dodecanyl; 2,4-diethylundecanyl; 2,2-dimethylpentyl; 1-methyl-cycloalkyl; 1-ethyl-cyclopentyl; cycloheptylmethylene; and 4-cyclopentyl-2,2-dimethylbutyl.

It is known to those skilled in the art that those amides of the present invention having an asymmetric carbon atom may exist in racemic or optically active rectus (R) or sinister (S) configurations. All of these forms are contemplated within the scope of this invention. The (S) configuration is preferred because it has the greatest activity.

A process for making compounds of the current invention is illustrated in Example 1. Other compounds are illustrated in Example 2.

EXAMPLE 1

A. (S)-3-Benzoylthioisobutyric acid; $[d]_D^{CHCl_3} = -61.90°$; obtained from Chemical Dynamics Corporation (27 g, 0.121 mmol) was dissolved in a mixture of methylene chloride (75 ml) and dimethylformamide (2.5 ml). Thionyl chloride (12.6 ml) was added dropwise. After all the thionyl chloride was added, the reaction mixture was stirred for four hours. Methylene chloride and excess thionyl chloride were evaporated in vacuo and the residue was dissolved in ether. The ether was washed twice with water, dried over magnesium sulfate, filtered and evaporated to afford (S)-2-benzoylthio-1-methylpropanoyl chloride as a pale yellow oil (16.0 g, 55%).

B. Tert-Butyl N-(cyclopentyl)glycine (12.9 g, 65 mmols) and triethylamine (6.5 g, 65 mmols) were added to methylene chloride (250 ml). The resulting solution was chilled in an ice bath. The compound of A. (16.0 g, 65 mmols) was added dropwise to the above chilled solution. The reaction mixture was stirred for thirty minutes with external cooling and then for two and a half hours at room temperature. The methylene chloride was washed twice with water, dried over magnesium sulfate, filtered and evaporated to give the product as initially a pale yellow oil (22.2 g, 84.4%). An analytical sample was prepared by chromatography over silica gel ($CHCl_3$) to give the pure product tert-butyl (S)-N-cyclopentyl-N-[3-(benzoylthio)-2-methyl-1-oxopropyl]glycinate as a colorless solid after crystallization form etherhexane; m.p. 54°–56°.

C. Nitrogen gas was bubbled through a methanolic solution (250 ml) of the product of B (21 g, 51.9 mmols) for half an hour followed by anhydrous ammonia for thirty minutes. The reaction mixture was stirred at room temperature under nitrogen for sixteen hours. The solvent was evaporated and the residue was dissolved in ethyl acetate. The ethyl acetate was washed with water, IN HCl, and again with water. The ethyl acetate was dried over magnesium sulfate, filtered and evaporated to afford the crude product. The crude product was purified by column chromatography over silica-gel (ethyl acetate/n-hexane, 5:95) to yield the pure product tert-butyl (S)-[N(3-mercapto-2-methylpropanoyl)-N-(cyclopentyl)]glycinate as a colorless oil (12.8, 82%) which was identical in all respects to that previously described.

D. To the mixture of the product of C (4.5 g, 15 mmols) and triethylamine (2 g, 20 mmols) in methylene chloride (150 ml) was slowly added under nitrogen a solution of pivaloyl chloride (2 g, 16 mmols) in methylene chloride (20 ml). The reaction mixture was stirred under nitrogen at room temperature for sixteen hours. The reaction mixture was washed consecutively with water IN HCl, and water. The organic phase was dried over magnesium sulfate, filtered and evaporated in vacuo to afford the crude product as a pale yellow oil. The crude product was purified by chromatography over silica-gel (ethyl acetate/hexane, 5:95) to give colorless crystals of tert-butyl (S)-N-cyclopentyl-N-[3-[(2,2-dimethyl-1-oxopropyl)thio]-2-methyl-1-oxopropyl]glycinate (5.5 g, 95%) after crystallization from ethyl acetate/n-nexane: m.p. 58°.

E. To an ice-cold solution of the product of D in methylene chloride (30 ml) was slowly added a solution of trimethylsilyl iodide (1.24 g, 6 mmols) in methylene chloride (10 ml) under nitrogen. The reaction mixture was stirred for one hour at room temperature. To the reaction mixture was added ice-water and the product was extracted into 5% aqueous sodium bicarbonate. The aqueous solution was acidified to pH 4 with hydrochloric acid and the product was extracted several times into ethyl acetate. The ethyl acetate was washed with water, dried over magnesium sulfate, filtered and evaporated to afford the pure product of (S)-N-Cyclopentyl-N-[3-[(2,2-dimethyl-1-oxopropyl)thio]-2-methyl-1-oxopropyl]glycine as a colorless crystalline solid: (1.5 g, 76.1%); m.p. 155°–156°, $[\alpha]_D^{CHCl_3} = -104.64°$.

EXAMPLE 2

The following compounds can be made in a manner similar to Example 1.
(S)-N-Cyclopentyl-N-[3-[(2,2-dimethyl-1-oxopropyl)thio]-2-methyl-1-oxopropyl]glycine
S-[N-Trimethylacetylthio-2-methylpropanoyl)-N-(toyl)]glycine
N-(3-(3,3-Dimethylbutyryl)thio-2-methylpropanyl)-N-cyclopropanoyl)-cyclopropyl glycine
S[N-Trimethylacetylthio-2-methylpropanoyl)-N-1-furfuryl]glycine
(DL)-[N-(3-Trimethylacetylthio-2-methylpropanoyl)-N-(exo-norbornyl)glycine
(DL)-N-(3-Trimethylacetylthio-2-methylpropanoyl)-N-phenyl glycine
(DL)-N-(2-tert-butylacetylthio-2-methylpropanoyl)-N-(p-tolyl)glycine
(DL)-[N-(3-tert-butylacetylthio-2-methylpropanoyl)-N-(2-indanyl)]glycine

EXAMPLE 3

The results of comparative stability studies are provided in the following:

COMPARISON 1

The following compounds were tested for stability in rat plasma.

$$R_7-S-\underset{\underset{H}{|}}{\overset{\overset{H}{|}}{C}}-\underset{\underset{CH_3}{|}}{\overset{\overset{H}{|}}{C}}-\underset{\overset{\|}{O}}{C}-N-\underset{\underset{H}{|}}{\overset{\overset{H}{|}}{C}}-\underset{\overset{\|}{O}}{C}-OH$$

| $R_7$ | M | $T\frac{1}{2}$ |
|---|---|---|
| 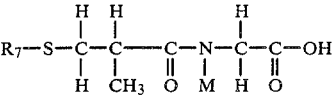 H₃CC— with =O | exo-Norbornyl | 3.8 hours |
| 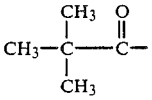 (CH₃)₃C—C(=O)— | exo-Norbornyl | over 22 hours |
| 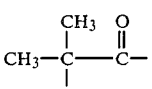 (CH₃)₃C—C(=O)— | Cyclopropyl | over 22 hours |

COMPARISON 2

The following compounds were tested for stability in 0.1N HCl solution at 37° C.

$$R_7-S-\underset{\underset{H}{|}}{\overset{\overset{H}{|}}{C}}-\underset{\underset{CH_3}{|}}{\overset{\overset{H}{|}}{C}}-\underset{\overset{\|}{O}}{C}-N-\underset{\underset{H}{|}}{\overset{\overset{H}{|}}{C}}-\underset{\overset{\|}{O}}{C}-OH$$

| $R_7$ | M | Degradation After 24 Hours |
|---|---|---|
| H₃C—C(=O)— | exo-Neobornyl | 15% |
| (CH₃)₃C—C(=O)— | Cyclohexyl | 0% |
| (CH₃)₃C—CH—C(=O)— (with H) | Cyclohexyl | 0% |
| (CH₃)₃C—C(=O)— | Cyclopentyl | 0% |

These comparisons show that compounds having an $R_7$ which is a branched alkanoyl are significantly and unexpectedly more stable than compounds having acetyl as $R_7$.

We claim:
1. Compounds of the structure

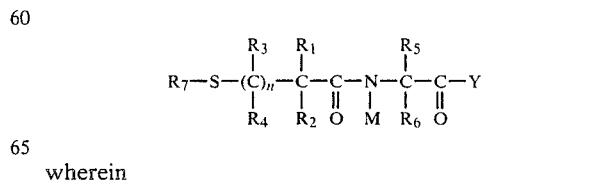

wherein
$R_1$, $R_2$, $R_3$, $R_4$ $R_5$ and $R_6$ are independently hydrogen, lower alkyl, lower alkenyl, lower alkynyl or phenyl-lower alkyl, wherein the lower alkyl, lower alkenyl and lower alkynyl groups have up to 6 carbon atoms, n is an integer from 0 to 4, M is cycloalkyl, cycloalkyl-lower alkyl, bicycloalkyl, fused arylcycloalkyl, lower alkylphenyl, hydroxyphenyl, methylenedioxyphenyl, bicycloalkyl-lower alkyl, halophenyl or alkylthiophenyl, and contains from 3 to 16 carbon atoms, Y is hydroxy, lower alkoxy having 1 to 6 carbon atoms or amino, $R_7$ is a group of the formula

wherein X is a branched alkane or a cycloalkyl or a cycloalkylloweralkyl, and where Y is hydroxy, their non-toxic pharmaceutically acceptable alkali metal, alkaline earth metal, and amine salts.

2. The compound of claim 1 wherein
$R_7$ is a group of the formula

wherein X is an alkane or cycloalkyl having 4 to 12 carbons.

3. The compound of claim 1 wherein
$R_7$ is a group of the formula

wherein X is an alkane or cycloalkyl having 4 to 8 carbons.

4. The compound of claim 1 wherein
$R_7$ is a group of the formula

wherein X is tert-butyl or 2,2-dimethylpropyl.

5. The compound of claim 1 wherein
$R_7$ is a group of the formula

wherein X is tert-butyl.

6. The compound of claim 2 wherein
$R_1$, $R_2$, $R_3$, $R_4$ and $R_6$ are independently H, $C_1$-$C_6$ alkenyl, $C_2$-$C_6$ alkynyl, phenyl-$C_1$-$C_6$ alkyl, or $C_3$-$C_6$ cycloalkyl.

7. The compound of claim 6 wherein M is $C_3$-16 cycloalkyl.

8. The compound of claim 6 wherein M is cyclopropyl, cyclobutyl, cyclopentyl, cyclohexyl, cycloheptyl or norbornyl.

9. The compound of claim 8 wherein
$R_1$, $R_3$, $R_4$, $R_5$ and $R_6$ are hydrogen,
$R_2$ is a $C_1$-$C_3$ alkyl,
n is 1, and
Y is hydroxy.

10. The compound of claim 9 wherein the alkane of $R_2$ is tert-butyl or 2,2-dimethylpropyl.

11. The compound of claim 1 is sinester (S) configuration.

12. The compound of claim 2 is sinester (S) configuration.

13. The compound of claim 10 is sinester (S) configuration.

14. The compound of claim 1 selected from the group consisting of
tert-butyl (S)-N-cyclopentyl-N-[3-[(2,2-dimethyl-1-oxopropyl)thio]-2-methyl-1-oxopropyl]glycinate,
(S)-N-cyclopentyl-N-[3-[(2,2-dimethyl-1-oxopropyl)thio]-2-methyl-1-oxopropyl]glycine,
(S)-N-cyclopentyl-N-[3-[(2,2-dimethyl-1-oxopropyl)thiol]-2-methyl-1-oxopropyl]glycine,
S-[N-trimethylacetylthio-2-methylpropanoyl)-N-(tolyl)]glycine
N-(3-(3,3-dimethylbutyryl)thio-2-methylpropanoyl-N-cyclopropanoyl)-cyclopropyl glycine,
[S[N-trimethylacetylthio-2-methylpropanoyl)-N-1-furfuryl]glycine,]
(DL)-[N-(3-trimethylacetylthio-2-methylpropanoyl)-N-(exonorbornyl)]glycine,
(DL)-[N-(3-trimethylacetylthio-2-methylpropanoyl)-N-(cyclopropyl)]glycine,
(DL)-[N-(3-trimethylacetylthio-2-methylpropanoyl)-N-(cyclopentyl)glycine],
(DL)-[N-(3-trimethylacetylthio-2-methylpropanoyl)-N-(cyclohexyl)glycine],
(DL)-N-(3-trimethylacetylthio-2-methylpropanoyl)-N-phenyl glycine,
(DL)-N-(2-tert-butylacetylthio-2-methylpropanoyl)-N-(p-tolyl)glycine,
.(DL)-N-(2-tert-butylacetylthio-2-methylpropanoyl)-N-(cyclohexyl)glycine, and
(DL)-[N-(3-tert-butylacetylthio-2-methylpropanoyl)-N-(2-indanyl)]glycine.

15. Compounds of the structure

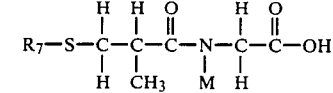

wherein
$R_7$ is trimethyl acetyl or tert-butyl acetyl and
M is cyclohexyl, cyclopentyl, exo-norbornyl or cyclopropyl.

16. (S)-N-Cyclopentyl-N-[3-[(2,2-dimethyl-1-oxopropyl)thio]-2-methyl-1-oxopropyl]glycine.

* * * * *